United States Patent [19]
Campbell et al.

[11] Patent Number: 4,952,724

[45] Date of Patent: Aug. 28, 1990

[54] PROCESS FOR PREPARATION OF ALPHA-ARYLOXY ACETIC ACIDS AND THEIR SALTS

[75] Inventors: Arthur L. Campbell, Glenview; Richard A. Mueller, Glencoe; John S. Ng, Chicago; Richard A, Partis, Evanston, all of Ill.

[73] Assignee: G. D. Searle & Co., Chicago, Ill.

[21] Appl. No.: 447,740

[22] Filed: Dec. 8, 1989

[51] Int. Cl.$^5$ .................... C07C 59/48; C07C 62/06; C07C 59/90

[52] U.S. Cl. .................... 562/471; 562/466; 562/469; 562/463

[58] Field of Search ................ 561/471, 466, 463, 469

[56] References Cited

U.S. PATENT DOCUMENTS

| | | | |
|---|---|---|---|
| 3,255,241 | 12/1966 | Schultz et al. | 562/471 |
| 3,918,899 | 2/1975 | Perrier et al. | 8/120 |
| 4,153,803 | 5/1979 | Thiele et al. | 562/471 |
| 4,173,709 | 11/1979 | Melivien et al. | 562/471 |
| 4,310,689 | 1/1982 | Eveleens et al. | 562/472 |
| 4,532,346 | 7/1985 | Rehn et al. | 562/471 |
| 4,711,903 | 6/1987 | Mueller et al. | 514/381 |
| 4,755,524 | 4/1988 | Mueller et al. | 514/381 |
| 4,804,777 | 1/1989 | Summer et al. | 562/421 |

FOREIGN PATENT DOCUMENTS 9285 2/1980 European Pat. Off. .

OTHER PUBLICATIONS

Fuson, et al., Organic Synthesis Collected Volumes, 2: 260–262 (1943).

*Primary Examiner*—Paul J. Killos
*Attorney, Agent, or Firm*—Mary Jo Kanady; Paul D. Matukaitis

[57] ABSTRACT

A process for producing aryloxy acetic acids and salts thereof which comprises reacting an alcohol of the formula R-OH wherein R is aryl or substituted aryl with a base in an aprotic organic solvent to give an aryloxide followed by removal of the organic solvent and reaction of the aryloxide with a salt of a monohaloacetic acid in a polar aprotic solvent such as DMSO to give the corresponding aryloxyacetate salt which then may be recovered or may optionally be converted to the corresponding acid by contacting the aryloxyacetate salt with an acid.

9 Claims, No Drawings

PROCESS FOR PREPARATION OF ALPHA-ARYLOXY ACETIC ACIDS AND THEIR SALTS

BACKGROUND OF THE INVENTION

1. Field of the Invention

The present invention relates to a novel one pot process for the preparation of an α-aryloxy acetic acid having the general formula $$RO\text{—}CH_2COOH$$

or a salt thereof, wherein R can be aryl which can optionally be substituted by one or more substituents selected from the group consisting of straight or branched chain alkyl, alkoxy, alkoxy alkyl, halo, phenyl, substituted phenyl, hydroxy, and 2-methylene-1-oxobutyl; which comprises reacting an alcohol of the formula $$R\text{—}OH$$

wherein R is defined as above, with a suitable base in an aprotic organic solvent to generate an aryloxide anion, removal of the organic solvent, and coupling of the aryloxide anion with a salt of a monohaloacetic acid in an aprotic polar solvent such as dimethyl sulfoxide (DMSO) to give the aryloxy acid salt which can be recovered or can optionally be reacted with acid to give the α-aryloxy acetic acid product. This process has the advantages of providing a high yield of product and being able to be conducted in one pot thus providing a quicker, more efficient and less costly synthesis. The process of the present invention permits the unexpectedly efficient and convenient preparation of α-aryloxy acetic acids in improved overall yield and purity.

(b) Prior Art

U.S. Pat. Nos. 4,711,903 and 4,755,524 disclose a method of preparing a [2-[[3,5 bis(1,1-dimethylethyl) 4-hydroxyphenyl]thio]-alkoxy]acetic acid from a 2,6-bis (1,1-dimethylethyl) 4-[(2 hydroxyalkyl) thio]phenol by a process in which chloroacetic acid is added to the alcohol in t-butyl alcohol which is a protic solvent, then potassium tert-butoxide is added, and the mixture is refluxed. This method gives yields of less than 25% and thus is not a very efficient process.

U.S. Pat. No. 4,804,777 discloses a process for the preparation of an aryloxy acetic acid by oxidation of an aryloxyethanol in an aqueous alkaline reaction medium at a temperature in the range of 0° C. to the boiling point of the reaction medium in the presence of a catalytic amount of a catalyst comprised of palladium, silver, and optionally antimony, and carbon to form the corresponding alkali metal ester and contacting the alkali metal with a mineral acid.

U.S. Pat. No. 3,918,899 discloses a method of preparing carboxymethylated cottons in non-aqueous media by reacting anhydrous sodium cellulosate with a salt of a monochloroacetate in an anhydrous DMSO solution.

R. C. Fuson and B. H. Wojcik, ORGANIC SYNTHESIS COLLECTED VOLUMES, 2:260–262(1943) discloses a three-step method for preparing ethoxyacetic acid from ethanol which is the substrate and the solvent (protic solvent).

SUMMARY OF THE INVENTION

The present invention relates to a process for preparing an α-aryloxy acetic acid of formula I $$RO\text{—}CH_2COOH \quad (I)$$

or a salt thereof, wherein R is aryl, or substituted aryl having one or more substituents selected from the group consisting of straight or branched chain alkyl of 1 to 6 carbon atoms, alkoxy of 1 to 6 carbon atoms, alkoxy alkyl wherein the alkyl moieties have 1 to 6 carbon atoms, halo, phenyl, substituted phenyl, hydroxy, and 2-methylene-1-oxobutyl; which comprises:

(a) reacting a compound of the formula $$R\text{—}OH \quad (II)$$

wherein R is defined as hereinbefore with a base in an aprotic organic solvent to form an aryloxide (b) removing the organic solvent;

(c) reacting the aryloxide with a salt of a monohaloacetic acid in an aprotic polar solvent to give an aryloxy acetate salt; and (d) optionally reacting the aryloxy acetate salt with an acid to give the α-aryloxy acetic acid of formula I.

DETAILED DESCRIPTION OF THE INVENTION

This invention relates to a process for preparing compounds of Formula I a previously described. The present invention further relates to a process for preparing an α-phenoxy acetic acid of the formula (I)

$$RO\text{—}CH_2COOH \quad (I)$$

or a salt thereof, wherein R is phenyl or substituted phenyl having one or more substituents selected from the group consisting of 1 to 4 carbon atoms, alkoxy of 1 to 4 carbon atoms, alkoxyalkyl wherein the alkyl moieties have 1 to 4 carbon atoms, halo, phenyl, substituted phenyl, hydroxy, and 2-methylene-1-oxobutyl; which comprises:

(a) reacting a compound of the formula $$R\text{—}OH \quad (II)$$

wherein R is defined as hereinbefore with a base in an aprotic organic solvent to form a phenoxide;

(b) removing the organic solvent; and (c) reacting the phenoxide with a salt of a monohaloacetic acid in an aprotic polar solvent to give phenoxy acetate salt which can be recovered as the salt or can optionally be reacted with an organic acid or mineral acid to give the phenoxy acetic acid product.

The process of the present invention can be conducted in one pot, thus fewer steps are required to produce the product. The process provides higher overall yields with fewer purification procedures being needed.

If the α-phenoxy acetic acid salt is desired it can be recovered as the product or optionally it can be reacted with an acid to give the α-phenoxy acetic acid as the final product.

In a preferred embodiment the process of the present invention can be used to prepare a compound of the formula

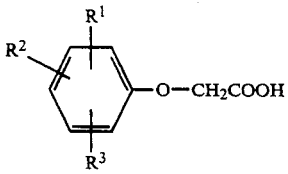

or salt thereof wherein $R^1$, $R^2$ and $R^3$ are the same or different and are hydrogen, alkyl of 1 to 4 carbon atoms, alkoxy of 1 to 4 carbon atoms, alkoxyalkyl wherein the alkyl moieties have 1 to 4 carbon atoms halo, phenyl, substituted phenyl, hydroxy, or 2-methylene-1-oxobutyl; by (a) reacting a compound of the formula

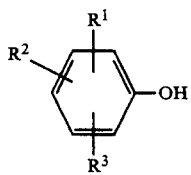

wherein $R^1$, $R^2$, and $R^3$ are defined as hereinbefore with a base such as sodium hydride in an aprotic organic solvent such as tetrahydrofuran to form a phenoxide of the formula

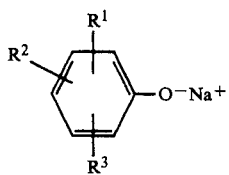

wherein $R^1$, $R^2$, and $R^3$ are as defined as hereinbefore;

(b) removing the organic solvent;

(c) reacting the phenoxide with a salt of a monohaloacetic acid, such as monochloroacetic acid, in a polar aprotic solvent, such as DMSO, to form a phenoxy acetate salt; and (d) reacting the phenoxy acetate salt with a mineral acid or organic acid to give the phenoxy acetic acid product.

Aprotic organic solvents suitable for use in the present invention include but are not limited to tetrahydrofuran (THF), ethers such as ethyl ether, t-butylmethyl ether, diisopropyl ether, and dioxane.

Polar aprotic solvents suitable for use in the present invention include but are not limited to dimethyl sulfoxide (DMSO), dimethylformamide (DMF), hexamethylphosphoramide (HMPA), sulfolane, dimethyl sulfone and tetramethylurea. Preferred solvents are dipolar aprotic solvents such as DMSO.

Monohaloacetic acid salts suitable for use in the present invention include but are not limited to the sodium, potassium, lithium, and cesium salts of monochloroacetic acid, monobromoacetic acid, and monoiodoacetic acid.

Suitable mineral acids and organic acids for acidifying the aryloxy acetate to the acid include but are not limited to hydrochloric acid, hydrobromic acid, hydrofluoric acid, sulfuric acid, nitric acid, acetic acid, trifluoroacetic acid, methanesulfonic acid, trifluoromethanesulfonic acid and phosphoric acid.

Suitable bases for reacting with the alcohol include but are not limited to sodium hydride, potassium hydride, calcium hydride, alkyllithiums, lithium dialkylamides, lithium bis(trimethylsilyl) amide, sodium bis(trimethylsilyl) amide, and potassium bis(trimethylsilyl) amide.

The reaction of the alcohol and base can be conducted over a broad temperature range, preferably from about $-50°$ C. to about $50°$ C. and most preferably from about $-15°$ C. to about $30°$ C.

The relative amounts of reactants used in the process can vary. Preferably an excess of base is reacted with the alcohol. In general the mole ratio of base to alcohol can be about 3 moles of base to about 1 mole of alcohol, preferably about 1.1 mole of base to about 1.0 moles of alcohol or alcohol equivalent such as an additional —OH group. In general, an excess of monohaloacetic acid salt is reacted with the alkoxide although the reaction can be conducted at a 1:1 molar ratio. Preferably, about 1.5 moles of monohaloacetic acid salt is reacted with the alkoxide intermediate.

The reaction to generate the aryloxide ion in the present process can be conducted over a broad temperature range, preferably from about $-50°$ C. to about $50°$ C. and most preferably from about $-15°$ C. to about $30°$ C.

The reaction of the aryloxide with a salt of a monohaloacetic acid can be conducted over a broad temperature range, preferably from about $0°$ C. to about $50°$ C. with about $10°$ C. to about $30°$ C. most preferred. The aryloxy acetate salt can be acidified to the acid over a broad temperature range, preferably from about $0°$ C. to about $50°$ C.

The term "alkyl", as used herein, refers to straight or branched chain alkyl groups having from 1 to 10 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "substituted phenyl" refers to phenyl having one or more substituents selected from the group consisting of halo, hydroxy, phenyl, lower alkyl and lower alkoxy.

The term "aryl" refers to phenyl, naphthyl, and the like.

The term "halo", as used herein in reference to aryl or phenyl substituents, includes chloro, bromo, iodo and fluoro.

The term "lower alkoxy" refers to alkoxy groups having from 1 to 6 straight or branched chain carbon atoms, i.e., methoxy, propoxy, tert butoxy, pentoxy, etc.

Scheme A illustrates the use of the process of the present invention for the preparation of α-aryloxy acetic acids of Formula I in which R is defined as hereinbefore from alcohols of Formula II by: (a) reacting the alcohol (II) with a base such as sodium hydride in an aprotic organic solvent such as tetrahydrofuran (THF) to form an aryloxide (IIa) followed by removal of the organic solvent and coupling of the aryloxide with a salt of a monohaloacetic acid such as sodium monochloroacetate in a polar aprotic solvent such as dimethyl sulfoxide (DMSO) to form the aryloxy acetate salt (IIb) which is converted to the aryloxy acetic acid (I) by reaction with an organic acid or a mineral acid such as hydrochloric acid.

Scheme B illustrates the preparation of substituted phenoxy acetic acids of Formula IV wherein $R^1$, $R^2$, and $R^3$, are defined as hereinbefore from alcohols of Formula III by the process of the present invention.

Scheme A

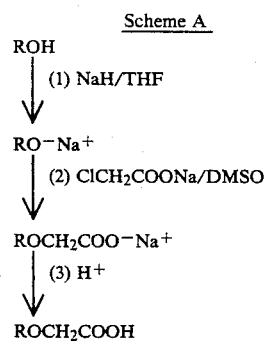

Scheme B

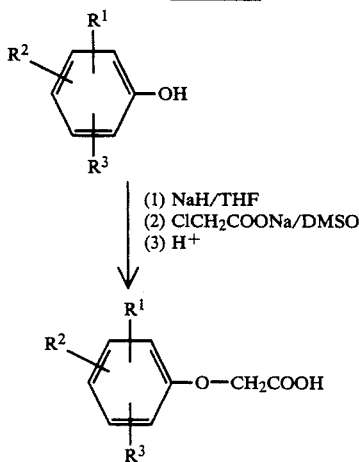

Compounds which can be prepared by the process of the present invention have a number of uses. For example ethacrynic acid is useful as a diuretic and phenoxy acetic acid is useful as a fungicide and a keratin exfoliative.

The following examples further illustrate the invention. All temperatures are degrees Celsius unless otherwise noted.

EXAMPLE 1

4-Methylphenoxyacetic acid

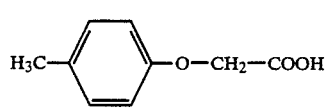

Sodium hydride (0.86 g of 60% NaH in oil=0.516 g, 21.5 mmol) in oil dispersion was washed twice with 10 ml of hexane. THF was added (5 ml) and the mixture was cooled to $-15°$ C. A solution of p-methylphenol (1.95 g, 18 mmol) in THF was then added, and the mixture was warmed to 25° C. for 1 hour. The THF was removed by distillation under vacuum and a solution of sodium chloroacetate (2.5 g, 22 mmol) in DMSO (50 ml) was added. The mixture was stirred at room temperature for 20 hours, then diluted with 300 ml. of water. The mixture was extracted twice with 50 ml. of hexane. The aqueous phase was acidified with 4N hydrochloric acid and the product was extracted twice with 100 ml. of ethyl acetate. The combined ethyl acetate layers were washed twice with 100 ml. water, dried over MgSO$_4$, filtered, and the solvent was removed by distillation under reduced pressure to give 2.9 g of product as a white solid. Yield of product=97.6%.

Example 2

[2,3-Dichloro-4-(2-methylene-1-oxobutyl)phenoxy]acetic acid (Ethacrynic Acid)

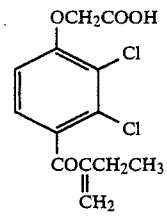

Substituting 2,3-dichloro(2-methylene-1-oxobutyl)-phenol for p-methylphenol and following the procedure of Example 1 gives the sodium salt of ethacrynic acid which is reacted with acid as in Example 1 to give ethacrynic acid.

Example 3

Phenoxyacetic acid

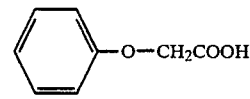

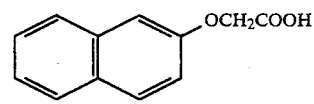

Substituting phenol for p-methylphenol and following the procedure of Example 1 gives the sodium salt of phenoxyacetate acid which is reacted with said acid as in Example 1 to give phenoxyacetate acid.

Example 4

2-Naphthoxyacetic Acid

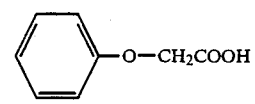

Substituting 2-naphthol for p-methylphenol and following the procedure of Example 1 gives the sodium salt of 2-naphthoxyacetate acid which is reacted with acid as in Example 1 to give 2-naphthoxyacetate acid.

What is claimed is:

1. A process for preparing a compound of the formula

RO—CH$_2$COOH          (I)

or a salt thereof, wherein R is aryl or substituted aryl having one or more substituents selected from the group consisting of straight or branched chain alkyl, alkoxy, alkoxyalkyl, halo, phenyl, substituted phenyl, hydroxy, and 2-methylene-1 oxobutyl; which comprises:

(a) reacting a compound of the formula

R—OH wherein R is defined as hereinbefore with a base in an aprotic organic solvent to form an aryloxide;
(b) removing the organic solvent;
(c) reacting the aryloxide with a salt of a monohaloacetic acid in an aprotic polar solvent to give an aryloxyacetate salt; and
(d) optionally reacting the aryloxyacetate salt with an acid.

2. A process according to claim 1 for preparing a compound of the formula

RO—CH$_2$COOH or a salt thereof wherein R is phenyl or substituted phenyl having one or more substituents selected from the group consisting of alkyl of 1 to 4 carbon atoms, alkoxy of 1 to 4 carbon atoms, alkoxyalkyl wherein the alkyl moieties have 1 to 4 carbon atoms, halo, phenyl substituted phenyl, hydroxy, and 2 methylene-1 oxobutyl; which comprises:
(a) reacting a compound of the formula

R—OH wherein, R is defined as hereinbefore, with a base in an aprotic organic solvent to form a phenoxide;
(b) removing the organic solvent;
(c) reacting the phenoxide with a salt of a monohaloacetic acid in an aprotic polar solvent to give a phenoxyacetate salt; and
(d) optionally- reacting the phenoxyacetate salt with an acid.

3. A process according to claim 2 for preparing a compound of the formula,

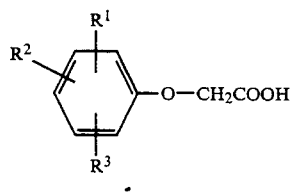

or a salt thereof wherein $R^1$, $R^2$, and $R^3$ are the same or different and are hydrogen, alkyl of 1 I to 4 carbon atoms, alkoxy of 1 to 4 carbon atoms, halo, phenyl, substituted phenyl, hydroxy or 2-methylene-1-oxobutyl; which comprises
(a) reacting a compound of the formula

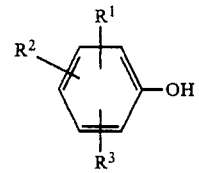

wherein $R^1$, $R^2$, and $R^3$ are defined as hereinbefore with a base in an aprotic organic solvent to form a phenoxide;
(b) removing the organic solvent;
(c) reacting the phenoxide with a salt of a monohaloacetic acid in an aprotic polar solvent to give a phenoxyacetate salt; and
(d) optionally reacting the phenoxyacetate salt with an acid.

4. A process according to claim 1 wherein the aprotic organic solvent is tetrahydrofuran and the aprotic polar solvent is dimethyl sulfoxide.

5. A process according to claim 2 wherein the aprotic organic solvent is tetrahydrofuran and the aprotic polar solvent is dimethyl sulfoxide.

6. A process according to claim 4 wherein the salt of a monohaloacetic acid is sodium chloroacetate.

7. A process according to claim 5 wherein the salt of a monohaloacetic acid is sodium chloroacetate.

8. A process according to claim 7 wherein the base is sodium hydride.

9. A process according to claim 2 for preparing 4-methylphenoxy acetic acid which comprises:
(a) reacting p-methylphenol with sodium hydride in tetrahydrofuran to form a phenoxide;
(b) removing the tetrahydrofuran;
(c) reacting the phenoxide with sodium chloroacetate in dimethyl sulfoxide to form a phenoxyacetate salt; and
(d) reacting the phenoxyacetate salt with hydrochloric acid.

* * * * *

UNITED STATES PATENT AND TRADEMARK OFFICE
CERTIFICATE OF CORRECTION

PATENT NO. : 4,952,724

DATED : Aug. 28, 1990

INVENTOR(S) : Campbell et al.

It is certified that error appears in the above-identified patent and that said Letters Patent is hereby corrected as shown below:

Column 2, line 29, reading "a previously" should read
-- as previously --.
Column 4, line 64, reading "hydrochlcric" should read
-- hydrochloric --.
Column 6, the third structure, should be deleted.
Column 6, the fourth structure, Example 4, should be deleted and should be replaced with the following structure:

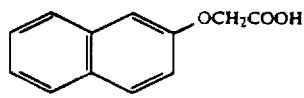

Column 6, line 56, reading "2-naphthoxyacetate" should read
-- 2-naphthoxyacetic --.
Column 7, line 22, reading "2 methylene-1 oxobutyl" should read
-- 2-methylene-1-oxobutyl --.
Column 8, line 2, reading "1 I to 4" should read -- 1 to 4 --.

Signed and Sealed this

Fourth Day of August, 1992

Attest:

DOUGLAS B. COMER

*Attesting Officer*     *Acting Commissioner of Patents and Trademarks*